United States Patent
Bernhard (10) Patent No.: US 9,435,729 B2
(45) Date of Patent: Sep. 6, 2016

(54) METHOD AND APPARATUS FOR DEGASSING A LIQUID AND ANALYTICAL DEVICE HAVING THE APPARATUS

(71) Applicant: Endress + Hauser Conducta Gesellschaft für Mess- und Regeltechnik mbH + Co. KG, Gerlingen (DE)

(72) Inventor: Ralf Bernhard, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 309 days.

(21) Appl. No.: 13/717,818

(22) Filed: Dec. 18, 2012

(65) Prior Publication Data
US 2013/0156646 A1    Jun. 20, 2013

(30) Foreign Application Priority Data
Dec. 19, 2011    (DE) .................. 10 2011 088 959

(51) Int. Cl.
*G01N 21/17*    (2006.01)
*B01D 19/00*    (2006.01)
*G01N 21/51*    (2006.01)

(52) U.S. Cl.
CPC ........... *G01N 21/17* (2013.01); *B01D 19/0036* (2013.01); *G01N 21/51* (2013.01)

(58) Field of Classification Search
CPC ... B01D 19/0036; G01N 21/51; G01N 21/17
See application file for complete search history.

(56) References Cited

U.S. PATENT DOCUMENTS

| | | | | |
|---|---|---|---|---|
| 5,112,575 A * | 5/1992 | Whitehouse | ......... | B01J 19/0046 422/110 |
| 5,183,486 A * | 2/1993 | Gatten | ............... | B01D 19/0031 210/198.2 |
| 5,772,736 A * | 6/1998 | van Schravendijk | ..... | B01D 19/0031 95/46 |
| 7,198,956 B2 | 4/2007 | Uffenheimer | | |
| 2002/0192113 A1 * | 12/2002 | Uffenheimer et al. | ......... | 422/67 |
| 2004/0163730 A1 * | 8/2004 | Olson | ................... | B01L 3/0206 141/130 |
| 2004/0223887 A1 * | 11/2004 | Bargh | ................ | B01D 19/0031 422/400 |
| 2004/0265185 A1 * | 12/2004 | Kitagawa | .............. | B01L 3/0268 422/400 |

(Continued)

FOREIGN PATENT DOCUMENTS

CN    201454165 U    5/2010
CN    202061423 U    12/2011

(Continued)

*Primary Examiner* — Shogo Sasaki
(74) *Attorney, Agent, or Firm* — Christopher R. Powers; PatServe (57) ABSTRACT

A method for degassing a liquid by means of a piston pump unit having a receiving chamber serving for accommodating the liquid to be degassed and connected with at least one supply line and at least one drain line, and a piston seated in the receiving chamber for performing stroke movements. The piston provides a liquid sealing of the receiving chamber on one end. The following steps are included: drawing liquid via the supply line into the receiving chamber by performing a first stroke movement of the piston in the case of blocked drain line and open supply line; producing a negative pressure in the receiving chamber by continuing the first stroke movement of the piston in the case of blocked supply line and blocked drain line; and opening the drain line and removing a gas phase present in the receiving chamber from the receiving chamber via the drain line by performing a second stroke movement of the piston directed counter to the first stroke movement in the case of an opened drain line and blocked supply line.

13 Claims, 1 Drawing Sheet

(56) References Cited

U.S. PATENT DOCUMENTS

| | | | |
|---|---|---|---|
| 2005/0056713 A1* | 3/2005 | Tisone | B01D 19/0047 239/690 |
| 2005/0140753 A1* | 6/2005 | Tsukahara | B41J 2/175 347/85 |
| 2006/0222569 A1* | 10/2006 | Barten | B01L 3/502 422/400 |
| 2006/0288803 A1* | 12/2006 | Weissgerber | G01N 30/36 73/865.8 |
| 2008/0227663 A1* | 9/2008 | Tisone | B01J 19/0046 506/39 |
| 2011/0259090 A1* | 10/2011 | Angelescu | G01N 33/2823 73/64.56 |
| 2012/0283457 A1* | 11/2012 | Du | B01D 11/0219 554/8 |
| 2013/0134095 A1* | 5/2013 | Anderer | B01D 15/1878 210/656 |

FOREIGN PATENT DOCUMENTS

| | | |
|---|---|---|
| DE | 2756965 | 6/1970 |
| JP | 57-132062 | 8/1982 |

* cited by examiner

METHOD AND APPARATUS FOR DEGASSING A LIQUID AND ANALYTICAL DEVICE HAVING THE APPARATUS

TECHNICAL FIELD

The invention relates to a method and an apparatus for degassing a liquid as well as to an analytical device comprising the apparatus for degassing the liquid.

BACKGROUND DISCUSSION

There are a large number of applications, for example, in the chemistry, biology, biotechnology, pharmacy and foods technology fields, in which liquids are used as solvents, as starting materials for a process or as reaction products. In many of these applications, the presence of dissolved gases and the therewith connected, possible forming of gas bubbles are undesirable. The forming of gas bubbles can, for example, interfere in the case of the chromatographic isolation of reaction products. Also, measurements of physical or chemical, measured variables in the liquids can be corrupted by the presence of gases or the forming of gas bubbles. Not only in laboratory methods but also in industrial processes, a precise and reliable measuring of certain measured variables is of great importance for both open and closed loop control of the processes and for quality assurance of the products.

In process measurements technology and in environmental technology, analytical devices are frequently applied for determining a measured variable of a liquid. For example, analytical devices can be applied for monitoring and optimizing the cleaning effectiveness of a clarification plant, for monitoring drinking water or for quality monitoring of food. Measured and monitored is, for example, the content of a certain substance (also referred to as the analyte) in the liquid sample. Analytes can include, for example, ions, such as ammonium, phosphate, silicate or nitrate, biological or biochemical compounds, e.g. hormones, or even microorganisms. Other measured variables, which are determined by analytical devices in process measurements technology, especially in the field of monitoring water, include the organic carbon content (TOC=total organic carbon) and the chemical oxygen demand (COD). Analytical devices can be embodied, for example, as cabinet devices or as buoys.

Frequently in analytical devices, the sample to be analyzed is treated by mixing with one or more reagents, so that a chemical reaction can occur in the liquid sample. In a number of analytical methods, the reagents are so selected that the chemical reaction is detectable by means of physical methods, for example, by optical measurements, or by means of potentiometric or amperometric sensors or by measuring conductivity. For example, the chemical reaction can bring about a coloring of the liquid sample, or a color change, which is detectable with optical means. The color intensity is, here, a measure for the measured variable to be determined. The measured variable can, in this case, be ascertained, for example, photometrically. Thus, electromagnetic radiation, for example, visible light, is radiated from a radiation source into the liquid sample and, after transmission through the liquid sample, is received by a suitable receiver. The receiver produces a measurement signal dependent on the intensity of the received radiation, from which the measured variable can be derived.

In order to use such analytical methods in an automated fashion, for example, for industrial applications or for monitoring a clarification plant or a body of water in the outdoors, it is desirable to provide an analytical device, which performs the required analytical method in an automated fashion. The most important requirements for such an analytical device are, besides a sufficient accuracy of measurement, robustness, simple serviceability and the assurance of a sufficient working, and environmental safety.

Semiautomatic and automatic analytical devices are known from the state of the art. Thus, for example, DE 102 22 822 A1, DE 102 20 829 A1 and DE 10 2009 029305 A1 disclose online-analyzers for analyzing samples. These online-analyzers are embodied, in each case, as cabinet devices, which include a control unit, supply containers for reagents, standards and cleaning liquids, pumps for transporting and dosing liquid samples, and the one or more reagents, into a measuring cell, and measuring transducers for optical measurements on the liquid sample treated with the one or more reagents in the measuring cell. The reagents, standards or cleaning liquids are transported from the supply containers and into the measuring cell. Correspondingly, used liquid is transferred from the measuring cell into a waste container.

The liquid sample to be analyzed contains, as a rule, dissolved gases, for example, air, or air components, such as oxygen, carbon dioxide and/or nitrogen. As a result of temperature- or pH changes of the liquid sample during the analytical method or due to chemical reactions when treating the liquid sample with reagents, such dissolved gases can form disturbing gas bubbles. Also, the reagents added to the liquid sample in the analytical device can contain dissolved gases and contribute in equal manner to gas bubble formation.

The presence of dissolved gases, or gas bubble formation, in the liquid sample can corrupt the analytical result ascertained by an analytical device. This is especially true in the case of the described photometric analytical method, in the case of which the liquid sample, pretreated by addition of reagents, and, in given cases, colored, absorbs light. The corruption results from gas bubbles present in the beam path of the measuring radiation radiated through the liquid sample.

In some analytical methods, gas is formed in a liquid sample treatment reaction between a reagent and the analyte or another chemical component of the liquid sample. This can serve for removing disturbing substances from the liquid sample. An example of this is the driving out of disturbing chloride ions from an aqueous liquid sample by the addition of concentrated sulfuric acid before determining the chemical oxygen demand of the sample by means of oxidation by potassium dichromate. This method is described, for example, in DE 10 2009 028165 A1. In the case of these methods, it is likewise of great importance for assuring a sufficient accuracy of measurement that the formed gases are removed from the liquid sample as completely as possible.

A gaseous component driven from the liquid sample can be, in other analytical methods, also a reaction product of the analyte. For example, a liquid sample can be mixed with lye for ascertaining the ammonium content. This converts ammonium to gaseous ammonia and, based on the arising amount of gas, the ammonium concentration of the liquid sample is deduced.

In the case of determining the organic carbon content of a liquid sample, frequently, the inorganic carbon fraction is driven out as carbon dioxide ($CO_2$), by acidification of the liquid sample, before the organic carbon fraction in the remaining liquid sample is oxidized to $CO_2$. A carrier gas stream is then fed through and the TOC content determined from the $CO_2$ concentration in the carrier gas stream.

Analytical devices for determining the total carbon content, the TOC content and/or the TIC content are known, for example, from DE 10 2008 025 877 A1, DE 10 2006 058 051 A1 or U.S. Pat. No. 5,340,542. Many TOC analytical devices also determine the inorganic carbon fraction (so-called TIC=total inorganic carbon) based on the amount of $CO_2$ arising from the inorganic carbon compounds of the liquid sample. Also in the case of these methods, it is important, for reaching a sufficient accuracy of measurement, that the gaseous component is separated as quantitatively as possible from the liquid sample, since, otherwise, an analyte concentration is ascertained, which is too low.

For removing gases from liquids used in laboratory applications, in process- and/or analytical technologies or from liquids obtained by chemical methods, often degassing apparatuses are applied. These are sometimes referred to as "degassers" or "debubblers".

Such an apparatus is described, for example, in U.S. Pat. No. 7,144,443 B2. The apparatus is integrated into a liquid carrying line and includes a tubular, gas- and liquid tight, outer jacket and a tubular, gas transmissive, inner line. The outer jacket has in its wall a connection to a vacuum source, which enables reduction of the pressure reigning in the annular space formed between the inner line and the outer jacket relative to the pressure reigning in the inner line. For degassing a liquid, such is transported through the inner line, while the vacuum source is applied to the space formed between the inner line and the outer jacket. Based on Henry's law, in this way, gas present in solution migrates through the wall of the inner line into the gas phase in the jacket and the liquid is, thus, degassed.

Disadvantageous in this procedure is, however, that the degassing apparatus requires, supplementally to a pump required for transporting the liquid through the inner line, a vacuum source, as well as a special separating diaphragm for the removal of the gas from the liquid. In many applications, such a method is not practical, not least of all in the above described analytical devices, which, depending on area of application, for example, in a clarification plant or at an environmental, analytical measuring point, should be able to function, as much as possible, without other peripheral devices, such as e.g., vacuum pumps.

SUMMARY OF THE INVENTION

It is therefore an object of the invention to provide a method and an apparatus for degassing a liquid as easily as possible.

This object is achieved by a method performed by means of a piston pump unit having a receiving chamber serving for accommodating the liquid to be degassed and connected with at least one supply line and at least one drain line, and a piston seated in the receiving chamber for performing stroke movements. The piston provides a liquid sealing of the receiving chamber on one end. The method comprises the steps of:

i. Drawing liquid via the supply line into the receiving chamber by performing a first stroke movement of the piston in the case of blocked drain line and open supply line;
ii. producing a negative pressure in the receiving chamber by continuing the first stroke movement of the piston in the case of blocked supply line and blocked drain line; and
iii. opening the drain line and removing a gas phase present in the receiving chamber from the receiving chamber via the drain line by performing a second stroke movement of the piston directed counter to the first stroke movement in the case of opened drain line and blocked supply line.

This method avoids the application of an additional vacuum source. Instead, a piston pump is applied for degassing the liquid, as well as equally serving for the transport of the liquid into the receiving chamber and for the further transport of the liquid from the receiving chamber after the degassing. This significantly simplifies the apparatus for performing the method.

In step ii., the negative pressure can be maintained for a predetermined time span. For this, the piston can, after the first stroke movement was continued until the piston achieved a predetermined end position, be held tightly in this end position in the case of retained blocked supply line and blocked drain line.

The liquid accommodated in the receiving chamber can be heated, especially during step ii. For example, the heating can occur during the holding of the negative pressure in the receiving chamber. The temperature increase decreases the solubility of gases in the liquid and, thus, amplifies the effect achieved by the applying of a negative pressure.

Steps ii. and iii can be performed multiple times, for example, 2 to 20 times, especially 2 to 5 times. The number of repetitions can be determined from the concrete method conditions, e.g. the volume to be degassed, the viscosity of the liquid to be degassed, the nature of the liquid and/or of the gas dissolved in the liquid and the application, for which the liquid is intended after the degassing.

The receiving chamber can be connected with a first drain line and a second drain line, wherein the gas phase is removed from the receiving chamber via the first drain line, and the liquid is transported further via the second drain line. The second drain line can be connected, for example, with a line or with a container, in which the liquid is brought together with one or more reaction partners, in order to perform a chemical reaction. The second drain line can also be connected with an inlet to a measuring device, which is embodied to determine a chemical or physical, measured variable of the degassed liquid. The measuring device can be, for example, a measuring cell of an analytical device, which determines concentration of a certain analyte or some other analytical parameter. Other analytical parameters can include, for example, total carbon content, TOC content and/or TIC, or the chemical oxygen demand of the liquid.

The gas removed via the first drain line from the receiving chamber can be discarded; it can, however, also be collected for additional analysis and/or fed to the analytical device.

For example, the pH value of the liquid can be so set before or after the drawing into the receiving chamber that a gaseous component is driven out of the liquid. Through one or more steps ii. and iii., the gaseous component can be largely quantitatively separated from the liquid and fed via the first drain line to a collection container and/or to the analytical device. The analytical device can ascertain the amount of the arising gaseous component and therefrom ascertain a parameter of the liquid, especially a concentration of an analyte.

If the analytical device is, for example, an analytical device for determining total carbon content, or the TOC content, of a liquid, acidification of the liquid can drive out the inorganically bound carbon as $CO_2$ and the occurring $CO_2$ amount determined as TIC content by the analytical device.

The apparatus for performing the above described method includes:
a piston pump unit having a receiving chamber serving for accommodating the liquid to be degassed and a piston movable in the receiving chamber. The piston provides a liquid sealing of the receiving chamber on one end;

at least one supply line connected with the receiving chamber;

at least one drain line connected with the receiving chamber;

a valve unit, especially one or more valves with associated control mechanisms or a multiport valve, by means of which the supply line and the drain line are selectively blockable, at least at times; and a control system, which is embodied to control the apparatus for performing the method.

For heating the liquid contained in the receiving chamber, the apparatus can include heating means. Such can be, especially, electrical heating elements, which convert electrical energy into heat, such as, for example, an electrical heating helical element, electrical heating tape, an electrical heating mantle, or the like.

The receiving chamber can be connected via the at least one supply line with a liquid supply, via a first drain line with a waste container for accommodating gas phase removed from the receiving chamber and via a second drain line with a receiving container for degassed liquid, wherein the valve unit, in a first state, connects the supply line with the receiving chamber and blocks the first and second drain lines, in a second state, blocks the supply line, the first drain line and the second drain line, in a third state, connects the waste container with the receiving chamber and blocks the supply line and the second drain line, and in a fourth state, connects the receiving container with the receiving chamber and blocks the supply line and the first drain line.

The valve unit can, in an especially simple embodiment, comprise a 4/4 valve.

The piston pump unit can comprise, for example, a syringe pump having a syringe cylinder and a syringe piston axially movably seated in the syringe cylinder and liquid sealing the syringe cylinder on one end. Arranged on the end of the syringe cylinder lying opposite the syringe piston can be a syringe outlet, which opens into the receiving chamber surrounded by the end of the syringe piston and the syringe cylinder. The syringe outlet can be connected via the valve unit, for example, via a 4/4 valve, with the liquid supply line, and with the first and second drain lines. If the valve unit is, for example, a 4/4 valve, this can connect the syringe outlet selectively with either the liquid supply line, the first drain line or the second drain line, while, simultaneously, the other two lines connected with the syringe outlet via the 4/4 valve are blocked from the receiving chamber, or also simultaneously block the syringe outlet from all lines connected with the syringe outlet via the 4/4 valve.

The here described apparatus can advantageously be integrated into an analytical device of the initially described field of the invention for determining a measured variable of a liquid sample. Such an analytical device for determining a measured variable of a liquid sample can furthermore comprise:

a processing system for treating the liquid sample, wherein the treating comprises adding at least one reagent to the liquid sample;

a measuring transducer for registering a measured value of the treated liquid sample correlated with the measured variable or a reaction product formed by treating the liquid sample;

a control unit, which is embodied to control the processing system; and an evaluating unit, which is embodied for determining the measured variable based on the measured value registered by the measuring transducer.

The analytical device can have one or more degassing apparatuses. In an embodiment, the analytical device can comprise, for example, a first degassing apparatus for degassing the liquid sample treated with the reagents before the registering of the measured variable. In another embodiment, the analytical device can have a degassing apparatus for degassing the untreated liquid sample and, in given cases, other degassing apparatuses for degassing one or more, especially all, of the reagents to be added to the liquid sample.

The processing system can be supplementally embodied to provide, in a measuring cell, the treated liquid sample or the reaction product formed by treating the liquid sample. In this embodiment, the measuring transducer can register, for the treated liquid sample contained in the measuring cell, the measured value correlated with the measured variable.

The control unit and the evaluating unit can be formed by a data processing system, for example, by a computer or a measurement transmitter. The functions of the control unit and the evaluating unit can be executed by a single data processing unit or distributed over a number of data processing units, which are connected with one another for communication. In an embodiment, the measuring device includes a computer, or a measurement transmitter, embodied to execute the functions of the control unit and the evaluating unit. For this, operating programs are stored in a data memory of the data processing unit, which can execute the operating programs to control the processing system and/or for determining the measured variable based on a signal received from the measuring transducer. The control- and/or evaluating unit can comprise the control system of the apparatus of the invention for degassing a liquid. If the analytical device has a computer or measurement transmitter, which performs the functions of the control unit and the evaluating unit, this can supplementally serve as control system of the apparatus.

The analytical device can have one or more supply containers, which contain reagents for treating the liquid sample. For supplying and metering the liquid sample and the reagents into the measuring cell, the analytical device can have one or more pumps, for example, syringe pumps. For example, the liquid sample and each reagent can have its own pump. The pumps are actuatable automatically by means of the control unit.

In an especially simple and space saving embodiment of the analytical device, the liquid to be degassed is transported by means of a syringe pump into the measuring cell, wherein the cylinder of the syringe pump, in which the syringe piston is axially movably seated and seals the cylinder liquid tightly at one end, serves as receiving chamber for accommodating the liquid to be degassed. In such case, the liquid to be degassed can be, for example, the untreated or treated liquid sample or a reagent. The syringe outlet arranged on the end of the syringe cylinder lying opposite the syringe piston can in this embodiment, be connected, on the one hand, with a supply line, via which the liquid to be degassed, thus the liquid sample or the reagent, can be drawn in, and, on the other hand, with a first drain line, via which the gas formed by applying a negative pressure in the syringe cylinder can be removed. Additionally, the syringe cylinder can be connected via its syringe outlet with a second drain line, via which the degassed liquid can be fed to a processing system for additional treating of the liquid sample or to the measuring cell. For intermittent blocking of the supply line, the first drain line and/or the second drain line for performing the above described method for degassing the liquid, a valve unit can be inserted between the syringe outlet and the supply line and the two drain lines, e.g. a 4/4 valve, as likewise described above. The 4/4 valve can be actuatable by means of the control unit of the analytical device.

The measuring transducer of the analytical device can be an optical, especially a photometric, measuring transducer, which includes at least one radiation source for electromagnetic radiation and a receiver, which is embodied to receive electromagnetic radiation emitted from the radiation source after transmission through the treated liquid sample and to output a measurement signal correlated with the intensity of the received radiation.

The analytical device can in another embodiment comprise means for determining a measured variable representing the concentration of an analyte contained in the liquid sample and converted into a gaseous reaction product by treating the liquid sample.

For example, the analytical device can be embodied to ascertain the TOC content of the liquid sample. For this, it can comprise a high temperature reactor for digesting the liquid sample and forming a gas mixture, which contains $CO_2$ formed from organically bound carbon of the liquid sample, and means for forming a carrier gas stream flowing through the high temperature reactor. The measuring transducer in this embodiment registers the concentration of $CO_2$ in the carrier gas stream. It can be arranged in the flow direction of the carrier gas stream behind the high temperature reactor. For ascertaining the inorganically bound, carbon fraction contained in the liquid sample, the analytical device can means have for acidifying the liquid sample before its introduction into the high temperature reactor, wherein the apparatus for degassing the liquid according to the above described method removes from the liquid the $CO_2$ formed after acidification of the liquid sample and transports such $CO_2$ via the first drain line connected with the receiving chamber into a container for volumetrically determining the arising amount of $CO_2$ or into the carrier gas stream of the analytical device. In the latter case, the TIC value of the liquid sample can be derived from the $CO_2$ concentration in the carrier gas stream. The second drain line of the apparatus for degassing the liquid is connected with an input of the high temperature reactor, in order to supply to the high temperature reactor the liquid sample after the separating of the $CO_2$ formed by conversion of the inorganic carbon fraction.

BRIEF DESCRIPTION OF THE DRAWINGS

The invention will now be explained in greater detail based on the examples of embodiments illustrated in the drawing, the figures of which show as follows.

DETAILED DISCUSSION IN CONJUNCTION WITH THE DRAWINGS

Figure 1:
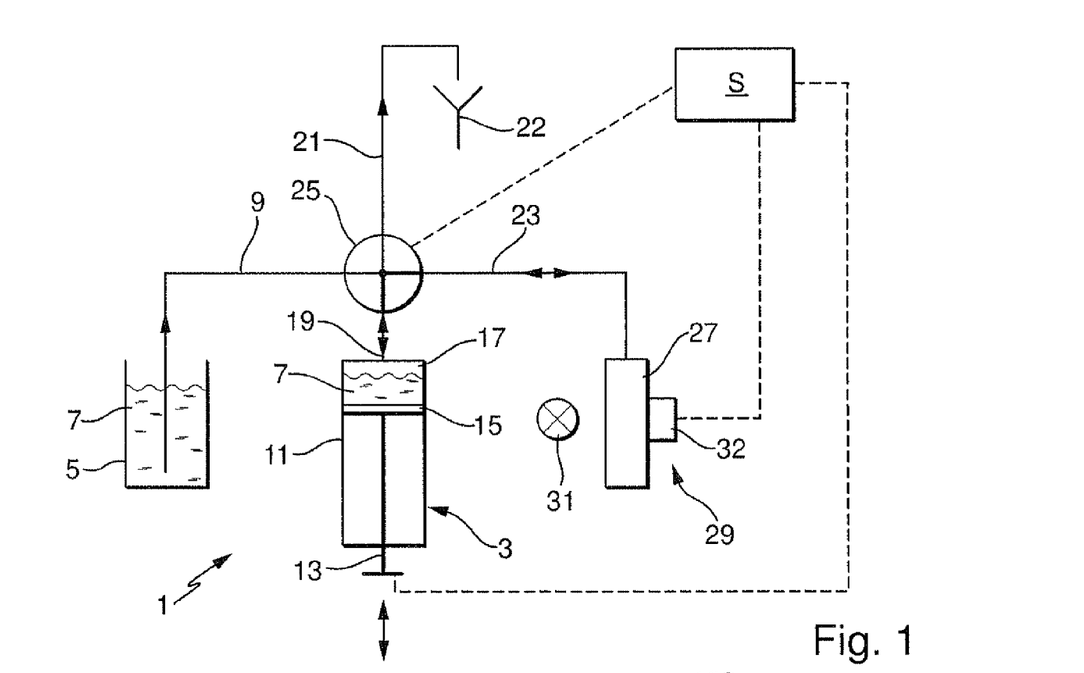
FIG. 1 is an apparatus for degassing a liquid.

FIG. 1 shows schematically an apparatus 1 for degassing a liquid 7. The liquid 7 is drawn by means of the piston pump 3 via the supply line 9 from the supply 5. Piston pump 3 is embodied in the example shown here as a syringe pump having a syringe cylinder 11 and a syringe piston 13 seated axially movably in the syringe cylinder 11. The syringe piston 13 bears at its periphery 15 liquid sealingly against the inner wall of the syringe cylinder 11 or is sealed by means of a sealing ring (not shown) bearing against the syringe cylinder 11, so that the syringe piston 13 liquid tightly seals the syringe cylinder 11 at one of the ends of the syringe cylinder 11. The space surrounded by the end of the syringe piston 13 and the syringe cylinder 11 forms a receiving chamber 17 for the liquid 7 to be degassed.

Arranged on the end of the syringe cylinder 11 lying opposite the syringe piston 13 and opening into the receiving chamber 17 is a syringe outlet 19, which is connected, via a valve unit in the form of a 4/4 valve 25, with the supply line 9, as well as with a first drain line 21 and a second drain line 23. Instead of a 4/4 valve, also another valve unit, such as one composed of a plurality of valves, i.e. one or more valves with associated control mechanisms, can be used.

The first drain line 21 connects the receiving chamber 17 with a waste container 22. The second drain line 23 connects the receiving chamber 17 with a measuring cell 27, which serves to accommodate liquid 7 after the degassing, so that a photometric measurement can be performed by means of an optical measuring transducer 29. The optical measuring transducer 29 includes a radiation source 31, which emits electromagnetic, measuring radiation, for example, visible light of one or more, defined wavelengths or a certain wavelength range. Additionally, the optical measuring transducer 29 includes a receiver 32, which receives measuring radiation transmitted through the liquid contained in the measuring cell 27 and outputs a measurement signal dependent on the received radiation intensity. The measurement signal is received and processed by a control unit connected with the measuring transducer 29 and embodied for registering measurement signals of the receiver 32 and for deriving from a measurement signal the measured variable. The radiation source 31 can comprise, for example, one or more light-emitting diodes (LEDs), each of which emits light of a different wavelength. Receiver 32 can have one or more photoelectric elements, especially one or more photodiodes or phototransistors. Measuring cell 27 can be formed, for example, of a material transparent for the measuring radiation. If the measuring radiation is visible light or UV radiation, the material for measuring cell 27 can be quartz glass, for example. Measuring cell 27 can also have optical windows for allowing the measuring radiation to pass through.

The apparatus further includes a control system S. Such can be, for example, a data processing system, especially a computer or a measurement transmitter. The data processing system includes a memory, in which one or more operating programs are stored, which, when they are executed by the data processing system, serve, among others things, for control of the syringe pump 3 and control of the 4/4 valve 25 for performing a method for degassing the liquid 7 by means of the apparatus 1. In the example shown here, control system S serves supplementally for controlling the optical measuring transducer 29 for performing a measurement and then evaluating the measurement signals output by the measuring transducer 29.

A method for degassing the liquid 7 by means of the apparatus 1 will now be described. In a first step, the liquid 7 is drawn by means of the piston pump 3 from the supply 5 into the receiving chamber 17. For this, the 4/4 valve 25 is brought into a first state, in which the syringe outlet 19 is connected with the supply line 9 and blocked from the drains 21 and 23, so that a transport of liquid 7 through the supply line 9 via the syringe outlet 19 into the receiving chamber 17 can take place, while a transport of liquid and/or gas through the drains 21 and 23 is, however, blocked. The suction for drawing liquid 7 into the receiving chamber 17 is provided by a stroke movement of the syringe piston 13. The stroke movement of the syringe piston 13 enlarges the receiving chamber 17, so that in the supply line 9 and the receiving chamber 17 a negative pressure forms and liquid 7 is drawn from the supply 5 and transported into the receiving chamber 17. The stroke movement is continued, until a predetermined amount of liquid 7 is located in the receiving chamber 17.

In a second step, the 4/4 valve 25 is brought into a second state, in which the syringe outlet 19 is connected neither with the supply line 9 nor with the drains 21, 23, so that transport of liquid and/or gas through the supply line 9 and the drains 21 and 23 is blocked. Receiving chamber 17 in this state of the 4/4 valve is thus sealed from the environment liquid- and gas tightly. By continuing the stroke movement of the syringe piston 13 in the same direction as that used for drawing the liquid 7 into the receiving chamber 17, a negative pressure is formed. In this way, according to Henry's law, the solubility of the gas dissolved in the liquid 7 is lessened, so that gas dissolved in the liquid 7 forms a gas phase in the receiving chamber 17. The negative pressure in the receiving chamber 17 can be maintained for some time. The apparatus 1 can optionally include heating means, with which the liquid 7 can be heated during the applying of the negative pressure, in order to strengthen the effect.

In a third step, the 4/4 valve 25 is brought into a third state, in which the syringe outlet 19 is connected with the first drain line 21 and blocked from the supply line 9 and the second drain line 23, so that gas- or liquid transport from the receiving chamber 17 to the waste container 22 is open, while gas- or liquid transport from the receiving chamber 17 back into the liquid supply 5 or into the measuring cell 27 is blocked. The gas phase formed in the receiving chamber 17 is then transported by means of a stroke movement of the syringe piston 13, in direction opposed to the previously performed stroke movements, into the waste container 22 (which can also be a gas measuring system).

Then, the second and third steps can be repeated one or more times.

In a following fourth step, the 4/4 valve 25 is brought into a fourth state, in which the syringe outlet 19 is connected with the second drain line 23 and blocked from the supply line 9 and the first drain line 21, so that liquid transport can occur from the receiving chamber 17 into the measuring cell 27, while liquid transport from the receiving chamber 17 into the waste container 22 or back into the supply 5 is, however, blocked. Through a further stroke movement of the syringe piston 13, especially a continuation of the stroke movement performed in the third step, the then degassed liquid 7 is transported from the receiving chamber 17 via the second drain line 23 into the measuring cell 27. A measurement on the degassed liquid 7 accommodated in the measuring cell 27 can then be performed by means of the measuring transducer 29.

The apparatus shown in FIG. 1 can be applied advantageously in a large number of applications. For example, it can be used for degassing liquids for laboratory- and industrial applications, especially for degassing educts for chemical methods or for degassing products of methods. It can, of course, as in the here described example, also be used for degassing liquids for measurements or analyses, however, also for chromatographic separation methods.

Figure 2:
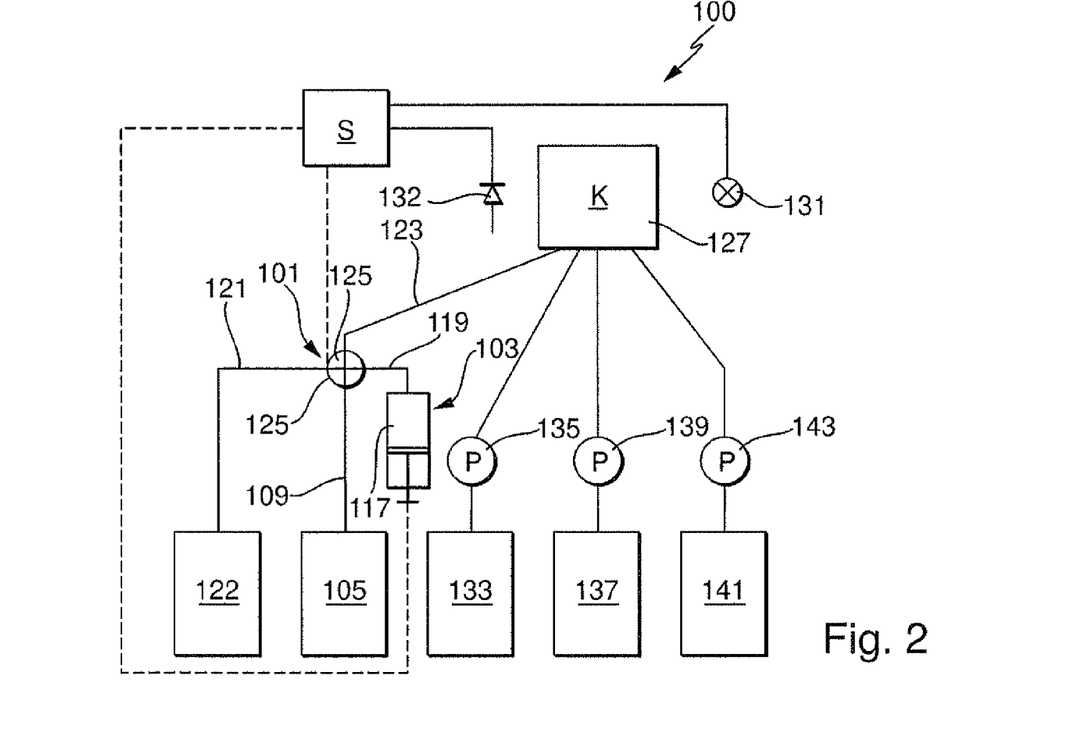
FIG. 2 is an analytical device for determining a measured variable of a liquid sample.

FIG. 2 shows, schematically, an analytical device 100 for determining a measured variable of a liquid. The analytical device 100 includes a number of supply containers 133, 137 and 141, and a processing system with a plurality of pumps 135, 139 and 143 for supplying and metering liquids contained in the supply containers 133, 137 and 141, and liquid lines, via which the supply container 133, 137, 141 are connected with a measuring cell 127. The pumps 135, 139 and 143 can be, for example, membrane pumps, piston pumps, especially syringe pumps, or peristaltic pumps. Furthermore, the analytical device 100 includes a sample supply 105 containing a liquid to be analyzed, which is, in given cases, filtered and conditioned using a sample preparation apparatus (not shown in FIG. 2) for the purpose of later analysis. The sample supply 105 is connected via the supply line 109 with an apparatus 101 for degassing the liquid to be analyzed. Apparatus 101 is embodied as already described based on FIG. 1 and includes a syringe pump 103, which forms a receiving chamber 117 for the liquid to be analyzed. Receiving chamber 117 is connectable via a 4/4 valve 125 selectively with the supply line 109, a first drain line 121 leading to a waste container 122 or a second drain line 123 leading to a measuring cell 127, or can be simultaneously blocked from all of these lines.

For registering the measured variable to be determined by the analytical device 100, the analytical device 100 further includes an optical measuring transducer, which includes a measuring radiation emitting, radiation source 132 and a receiver 131, which are so arranged relative to the measuring radiation transparent, measuring cell 127 that the measuring radiation passes through a liquid sample contained in the measuring cell 127 and the measuring radiation that has passed through the liquid lands on the receiver 131.

The analytical device 100 can be operated completely automatically. To accomplish this, it possesses a control unit S, which, in the example shown here, also the functions as an evaluating unit, especially for determining a measured variable based on a measured value registered by the measuring transducer. In the example shown here, control unit S serves, moreover, to control the apparatus 101 for degassing the liquid to be analyzed in the manner already described based on FIG. 1. Control unit S includes a data processing system, which can be embodied analogously to the data processing system applied in the example according to FIG. 1. The data processing system can also include an input apparatus for input of commands or parameters by a service person and/or an interface for the receipt of commands, parameters or other data from a superordinated unit, for example, from a process control system. Additionally, the control unit S can also include an output apparatus for output of data, especially measurement results, or operating information, to a user or even include an interface for output of data to the superordinated unit. Control unit S is connected with drives of the pumps 103, 135, 139, 143 and with valves (not shown), in order to operate such for transporting liquids from the sample supply 105 and the supply containers 133, 137 and 141 into the measuring cell 127 in an automated fashion. Control unit S is, moreover, connected with the measuring transducer, in order to control such and to ascertain the measured variable from measurement signals of the receiver 132.

Supply container 141 can contain a reagent, which is mixed with the sample liquid transported from the supply 105 for treating such sample liquid. If the variable to be determined is, for example, the concentration of an analyte in the liquid, the reagent can be so selected that it reacts with the analyte to form a colored reaction product. The intensity of the color is then a measure for the concentration to be determined. The wavelength of the measuring radiation transmitted by the radiation source 132 is, in this case, matched to the color of the reaction product and is correspondingly evaluated by the receiver 131, respectively the control unit. Instead of a single reagent as in the example shown here, depending on measured variable to be determined, also a plurality of reagents can be applied. In this case, the analytical device 100 has a corresponding number of supply containers for the required reagents.

In measurement operation of the analytical device 100, the control unit S first provides that a predetermined amount of the liquid contained in the sample supply 105 flows into the receiving chamber 117 of the syringe pump 103. There, the liquid is degassed by means of the syringe pump 103 in cooperation with the 4/4 valve 125 in the manner described at length based on FIG. 1, whereupon the gas phase formed under negative pressure in the receiving chamber 117 is transported via the first drain line 121 into the waste container 122. Then, a predetermined amount of the degassed liquid present in the receiving chamber 117 is metered by means of the syringe pump 103 via the second drain line 123 into the measuring cell 127 as liquid sample to be analyzed. At the same time, or thereupon, the control unit S controls the pump 143, in order to transport a predetermined amount of the reagent contained in the supply container 141 into the measuring cell. Measuring cell 127 serves thus in the here described example also as mixing cell, in which the liquid sample and reagent are mixed with one another. There are, however, also other embodiments possible, in which the reagent or a plurality of reagents for treating the liquid sample are mixed with one another before the liquid sample treated by means of the reagents is metered into the measuring cell 127.

For registering the measured variable to be determined for the treated liquid sample contained in the measuring cell, the control unit S operates the measuring transducer 131, 132 and evaluates the measurement signal output by the measuring transducer 131, 132. The measured variable ascertained from the measurement signal by the control unit S can be stored in a data memory of the control unit, and/or output via an interface to a superordinated unit and/or via a display of the control unit S.

After determining the measured variable, the measuring cell 127 is emptied. The used liquid sample can be transported, for example, into the waste container 122. The analytical device 100 has other supply containers 133, 137, which can contain standard solutions for calibrations and/or cleaning solutions for cleaning. By means of the pumps 135, 139 associated with the supply containers 133, 137, their solutions can be transported into the measuring cell 127.

After one or more completed measuring cycles, a calibrating of the analytical device can be performed by transporting a calibration standard from the supply container 137 into the measuring cell 127. The calibration standard is treated, like a "real" liquid sample from the sample supply, in the measuring cell 127 with reagent transported by means of pump 143 from the supply container 141 into the measuring cell 127. By means of the measuring transducer 131, 132, a measured value of the measured variable is photometrically determined and, in given cases, based on the measured value known for the calibration standard, an adjusting of the analytical device 100 is performed.

In the example shown here, the analytical device 100 has only one apparatus 101 for degassing a liquid. This apparatus 101 serves for removing disturbing dissolved gas from the liquid to be analyzed. In other embodiments, the analytical device can use also other such apparatuses, in order to remove dissolved gas also from one or more reagents and/or from the calibration standard.

An option is also to provide for the treated liquid, directly before its supply line to the measuring cell or to another measuring unit, an apparatus for degassing the treated liquid. For example, the liquid can be fed a treating reagent that effects a chemical conversion of the analyte to a gaseous reaction product. For example, for determining ammonium concentration, the liquid sample can be treated with a base, e.g. an NaOH solution, so that ammonia gas is formed. For determining a TIC content of a liquid sample, it can be acidified, in order to convert inorganic carbon compounds present in the liquid, e.g. carbonates, into gaseous $CO_2$. The so formed gas can be separated from the liquid by means of an apparatus for degassing a liquid, such as the apparatus 1 described based on FIG. 1, and instead of being sent to a waste container, be fed to the analytical device. The analytical device is embodied in this example of an embodiment to determine the amount of gas supplied to it. For example, the analytical device can, for this purpose, have a means for producing a gas stream of a carrier gas inert relative to the gas formed from the analyte, as well as a measuring transducer for determining the concentration of the gas in the carrier gas stream. The gas separated from the liquid can be supplied from the apparatus 1 by means of the piston pump 3 via the first drain line 21 to the carrier gas stream. This method can be performed completely automatically by means of the control unit S.

Besides the here described analytical methods and analytical devices, there are a large number of additional examples of embodiments and variations possible. Fundamentally, any type of treatment of a liquid in an analytical device can lead to gas production. Correspondingly, an apparatus of the invention for degassing a liquid can be applied at any number of locations within a processing system of an automatic analytical device.

The invention claimed is:

1. An apparatus for performing a method for degassing a liquid comprising:
   a piston pump unit comprising a receiving chamber serving for accommodating a liquid to be degassed;
   a piston movable in said receiving chamber and sealing said receiving chamber on one end;
   a liquid supply comprising the liquid to be degassed;
   at least one supply line connecting said receiving chamber with said liquid supply;
   at least a first drain, line connected with said receiving chamber;
   a valve unit, by means of which said at least one supply line and said first drain line are selectively blockable, at least at times; and
   a control unit configured to control the apparatus for performing the method for degassing a liquid comprising the steps:
      controlling the valve unit to block said first drain line and to connect said liquid supply via the at least one supply line with the receiving chamber and controlling the piston to perform a first stroke movement of the piston and to draw the liquid from said liquid supply via said at least one supply line into the receiving chamber;
      controlling the valve unit to block both said first drain line and said at least one supply line and controlling the piston to continue the first stroke movement in such a way, that a negative pressure is produced in the receiving chamber;
      controlling the valve unit to open said first drain line and to block said at least one supply line and controlling the piston to perform a second stroke movement in direction opposed to the first stroke movement and to remove a gas phase present in the receiving chamber from said receiving chamber via said first drain line.

2. The apparatus as claimed in claim 1, further comprising:
heating means for heating liquid contained in said receiving chamber.

3. The apparatus as claimed in claim 1, further comprising:
a waste container;
a second drain line, and
a receiving container, wherein:
said receiving chamber is connected via said first drain line with said waste container for accommodating the gas phase removed from said receiving chamber, and via the second drain line with said receiving container for the degassed liquid.

4. The apparatus as claimed in claim 3, wherein:
said valve unit comprises a 4/4 valve.

5. The apparatus according to claim 1,
said valve unit comprising one of: one or more valves with associated control mechanisms.

6. The apparatus according to claim 3,
said valve unit comprising one of: one or more valves with associated control mechanisms or a multiport valve.

7. The apparatus as claimed in claim 3,
said valve unit comprising a multiport valve, which is configured to be actuated by the control unit to be set into four different states, wherein:
in a first state, said multiport valve connects said liquid supply via said at least one supply line with said receiving chamber and blocks said first and second drain lines,
in a second state, said multiport valve blocks said at least one supply line, said first drain line and said second drain line,
in a third state, said multiport valve connects said waste container with said receiving chamber via said first drain line and blocks said at least one supply line and said second drain line,
in a fourth state, said multiport valve connects said receiving container with said receiving chamber via said at least second drain line and blocks said at least one supply line and said first drain line.

8. The apparatus as claimed in claim 1, wherein:
said piston pump comprises a syringe cylinder and said piston is axially movably seated in the syringe cylinder, said receiving chamber is surrounded by the syringe piston and the syringe cylinder and said syringe cylinder comprises a syringe outlet which opens ihto the receiving chamber.

9. The apparatus as claimed in claim 7,
said syringe outlet is connected with the liquid supply line and the first drain line via the valve unit.

10. The apparatus as claimed in claim 3, wherein:
said piston pump comprises a syringe cylinder and said piston is axially movably seated in the syringe cylinder,
said receiving chamber is surrounded by the syringe piston and the syringe cylinder and said syringe cylinder comprises a syringe outlet which opens into the receiving chamber, and
said syringe outlet is connected with the liquid supply line and the first and second drain lines via the valve unit.

11. The apparatus as claimed in claim 10, further comprising:
a receiving container;
a second drain line connecting the receiving container and the receiving chamber via said valve unit;
and said valve unit is configured to be actuated by the control unit to be set into a forth state, in which said valve unit connects said receiving container with said receiving chamber via said at least second drainline and blocks said at least one supply line and said first drain line.

12. The apparatus as claimed in claim 10, wherein:
said valve unit comprising one of: one or more valves with associated control mechanisms or a multiport valve.

13. The apparatus as claimed in claim 10, wherein:
the control unit is configured to control the apparatus for performing the method for degassing the liquid comprising the steps:
setting the valve unit in said first state and controlling the piston to perform a first stroke movement of the piston and to draw the liquid from said liquid supply via said at least one supply line into the receiving chamber;
setting the valve unit in said second state and controlling the piston to continue the first stroke movement in such a way, that a negative pressure is produced in the receiving chamber;
setting the valve unit in said third state and controlling the piston to perform a second stroke movement in direction opposed to the first stroke movement and to remove a gas phase present in the receiving chamber from said receiving chamber via said first drain line.

* * * * *

UNITED STATES PATENT AND TRADEMARK OFFICE
CERTIFICATE OF CORRECTION

PATENT NO. : 9,435,729 B2
APPLICATION NO. : 13/717818
DATED : September 6, 2016
INVENTOR(S) : Bernhard et al.

Page 1 of 1

It is certified that error appears in the above-identified patent and that said Letters Patent is hereby corrected as shown below:

Please add these inventors in this order (72): Ralf Bernhard, Stuttgart (DE); Ulrich Kathe, Ludwigsburg (DE); Lydia Hoppe, Ditzingen (DE)

Signed and Sealed this
Twenty-second Day of May, 2018

Andrei Iancu
*Director of the United States Patent and Trademark Office*